(12) United States Patent
Richlin et al.

(10) Patent No.: US 7,666,914 B2
(45) Date of Patent: Feb. 23, 2010

(54) TOPICAL PREPARATION AND METHOD FOR TRANSDERMAL DELIVERY AND LOCALIZATION OF THERAPEUTIC AGENTS

(76) Inventors: David M. Richlin, 5 Ashley Dr., Flanders, NJ (US) 07836; George R. Doherty, 41 Mountain Rd., Hadley, NY (US) 12835

( * ) Notice: Subject to any disclaimer, the term of this patent is extended or adjusted under 35 U.S.C. 154(b) by 1170 days.

(21) Appl. No.: 10/709,880

(22) Filed: Jun. 3, 2004

(65) Prior Publication Data

US 2004/0208914 A1    Oct. 21, 2004

(51) Int. Cl.
*A61K 9/06* (2006.01)
*A61K 9/08* (2006.01)
*A61K 9/10* (2006.01)
*A61K 45/06* (2006.01)
*A61K 45/08* (2006.01)

(52) U.S. Cl. .................. 514/947; 514/946; 514/886; 514/887; 514/930; 514/936; 514/816; 514/817; 514/818; 514/569; 514/557; 424/428; 424/429

(58) Field of Classification Search ............... 424/428, 424/429; 514/569, 557, 946, 947, 886, 887, 514/930, 816, 817, 818
See application file for complete search history.

(56) References Cited

U.S. PATENT DOCUMENTS

| | | | | |
|---|---|---|---|---|
| 3,551,554 A | 12/1970 | Herschler | ............... | 424/9.4 |
| 3,953,599 A | 4/1976 | MacMillan et al. | ......... | 514/304 |
| 4,379,792 A | 4/1983 | Blaine | ............... | 514/369 |
| 4,659,714 A | 4/1987 | Watt-Smith | | |
| 4,783,450 A | 11/1988 | Fawzi et al. | ............... | 514/78 |
| 4,847,250 A | 7/1989 | Alexander et al. | ........... | 514/247 |
| 4,933,184 A | 6/1990 | Tsuk | ............... | 424/449 |
| 4,960,771 A | 10/1990 | Rajadhyaksha | .......... | 514/228.8 |
| 4,963,367 A | 10/1990 | Ecanow | ............... | 424/485 |
| 5,059,603 A * | 10/1991 | Rubin | ............... | 514/263.31 |
| 5,167,616 A | 12/1992 | Haak et al. | ............... | 604/20 |
| 5,188,837 A | 2/1993 | Domb | ............... | 424/450 |
| 5,234,957 A | 8/1993 | Mantelle | ............... | 514/772.6 |
| 5,326,566 A | 7/1994 | Parab | ............... | 424/401 |
| 5,331,000 A | 7/1994 | Young et al. | ............... | 514/570 |
| 5,332,576 A | 7/1994 | Mantelle | ............... | 424/443 |
| 5,334,138 A * | 8/1994 | Sage et al. | ............... | 604/20 |
| 5,368,860 A | 11/1994 | Sunami et al. | ............... | 424/448 |
| 5,434,144 A * | 7/1995 | Kasting et al. | ............... | 514/76 |
| 5,443,829 A | 8/1995 | Kensil et al. | ............... | 424/765 |
| 5,446,070 A | 8/1995 | Mantelle | ............... | 514/772.6 |
| 5,482,965 A | 1/1996 | Rajadhyaksha | ............... | 514/452 |
| 5,601,838 A | 2/1997 | Hind | ............... | 424/443 |
| 5,613,958 A | 3/1997 | Kochinke et al. | ............... | 604/307 |
| 5,650,398 A | 7/1997 | Kensil et al. | ............... | 514/25 |
| 5,654,337 A | 8/1997 | Roentsch et al. | ............... | 514/570 |
| 5,719,197 A | 2/1998 | Kanios et al. | ............... | 514/772.6 |
| 5,750,141 A | 5/1998 | Roberts et al. | ............... | 424/449 |
| 5,780,051 A | 7/1998 | Eswara et al. | ............... | 424/449 |
| 5,807,568 A | 9/1998 | Cody et al. | ............... | 424/444 |
| 5,820,877 A | 10/1998 | Yamaguchi et al. | ............... | 424/449 |
| 5,837,289 A | 11/1998 | Grasela et al. | ............... | 424/484 |
| 5,849,737 A | 12/1998 | Chaplan et al. | ............... | 514/238.8 |
| 5,891,463 A | 4/1999 | Bello et al. | ............... | 424/449 |
| 5,900,249 A | 5/1999 | Smith | ............... | 424/443 |
| 5,942,241 A | 8/1999 | Chasin et al. | ............... | 424/426 |
| 5,948,389 A | 9/1999 | Stein | ............... | 424/45 |
| 5,976,547 A | 11/1999 | Archer et al. | ............... | 424/742 |
| 5,976,566 A | 11/1999 | Samour et al. | ............... | 424/449 |
| 5,985,317 A | 11/1999 | Venkateshwaran et al. | .. | 424/449 |
| 5,985,860 A | 11/1999 | Toppo | ............... | 514/159 |
| 5,993,836 A * | 11/1999 | Castillo | ............... | 424/401 |
| 5,993,849 A | 11/1999 | Assmus et al. | ............... | 424/449 |
| 6,007,843 A | 12/1999 | Drizen et al. | ............... | 424/488 |
| 6,576,791 B1 | 6/2003 | Axt et al. | ............... | 564/157 |
| 6,611,706 B2 | 8/2003 | Avrahami et al. | ............... | 604/20 |
| 6,638,981 B2 | 10/2003 | Williams et al. | | |
| 6,645,980 B1 | 11/2003 | Cuny et al. | ............... | 514/312 |
| 6,677,332 B1 | 1/2004 | Cuny et al. | ............... | 514/212.02 |
| 6,709,706 B2 | 3/2004 | Zhong et al. | ............... | 427/333 |
| 6,721,603 B2 | 4/2004 | Zabara et al. | ............... | 607/46 |
| 6,723,345 B2 | 4/2004 | Drizen et al. | ............... | 424/484 |
| 6,756,052 B1 | 6/2004 | Koch et al. | ............... | 424/448 |
| 7,273,887 B1 * | 9/2007 | Wepfer | ............... | 514/535 |
| 2002/0004481 A1 | 1/2002 | Cleland et al. | ............... | 514/12 |
| 2002/0037319 A1 | 3/2002 | Drizen et al. | ............... | 424/488 |

(Continued)

OTHER PUBLICATIONS

Williams et al. Advanced Drug Delivery Reviews 2004, 56, 603-618.*
A.L. Sisk Anesth. Prog. 1992, 39, 187-193.*
Potter et al. (Anesthesiology 1946, 7, 499-504).*
Ahad et al. Exp. Opin. Ther. Patents 2009, 19(7), 969-988.*
H.A.E. Benson Current Drug Delivery 2005, 2, 23-33.*
Brandao et al. Chapter 35 from Contact Dermatitis, Springer Berlin Heidelberg (Publisher), 4th Ed., 2006, Frosch, Menne, & Lepoittevin (Editors).*

(Continued)

*Primary Examiner*—Rebecca L Anderson
*Assistant Examiner*—Jason M Nolan
(74) *Attorney, Agent, or Firm*—Jay R. Yablon

(57) ABSTRACT

Disclosed herein is a preparation for topically delivering and localizing therapeutic agents, comprising: a vasoconstrictor for retarding vascular dispersion of a therapeutic agent; and a penetration enhancer for facilitating penetration of the vasoconstrictor and the therapeutic agent through a patient's skin. Further disclosed is an associated method of topically delivering and localizing therapeutic agents, comprising the steps of: using a vasoconstrictor for retarding vascular dispersion of a therapeutic agent; in combination with using a penetration enhancer for facilitating penetration of the vasoconstrictor and the therapeutic agent through a patient's skin. Also disclosed are various courses of treatment which comprise applying the various disclosed combinations of agents to the patient's skin.

150 Claims, 1 Drawing Sheet

U.S. PATENT DOCUMENTS

| | | | |
|---|---|---|---|
| 2002/0052319 A1 | 5/2002 | Pasternak et al. | 514/12 |
| 2002/0136788 A1 | 9/2002 | Quezada | 424/742 |
| 2002/0168412 A1 | 11/2002 | Drizen et al. | 424/488 |
| 2002/0176892 A1 | 11/2002 | Drizen et al. | 424/488 |
| 2003/0012830 A1 | 1/2003 | Small | 424/727 |
| 2003/0118651 A1 | 6/2003 | Jampani | 424/473 |
| 2003/0161867 A1 | 8/2003 | Lu et al. | 424/449 |
| 2004/0076648 A1 | 4/2004 | Williams et al. | |
| 2004/0087520 A1 | 5/2004 | Chowdhury et al. | 514/35 |
| 2004/0126415 A1 | 7/2004 | Lu et al. | 424/449 |
| 2004/0127531 A1 | 7/2004 | Lu et al. | 514/378 |
| 2004/0142911 A1 | 7/2004 | Small | 514/159 |
| 2004/0146590 A1 | 7/2004 | Iadarola | 424/760 |
| 2004/0151784 A1 | 8/2004 | Varadhachary | 424/687 |

OTHER PUBLICATIONS

Babar et al. Drug Development and Industrial Pharmacy 1990, 16(3), 523-540.*

Freeman et al. (1986). Efficacy of topical treatment for herpes simplex virus infections: predictions from an index of drug characteristics in vitro. University of Chicago Press, Journal of Infectious Diseases. vol. 153, pp. 64-70.

* cited by examiner

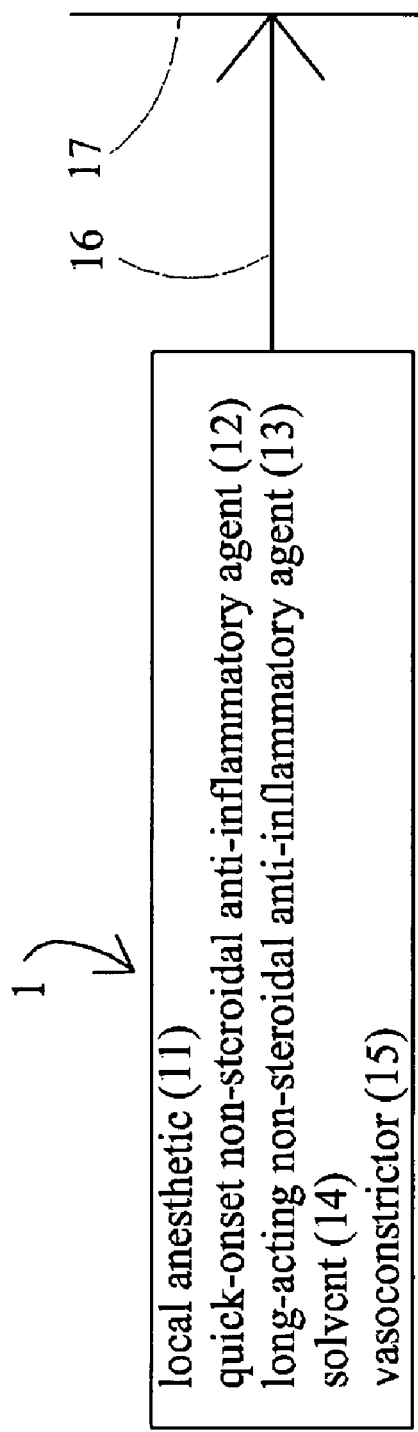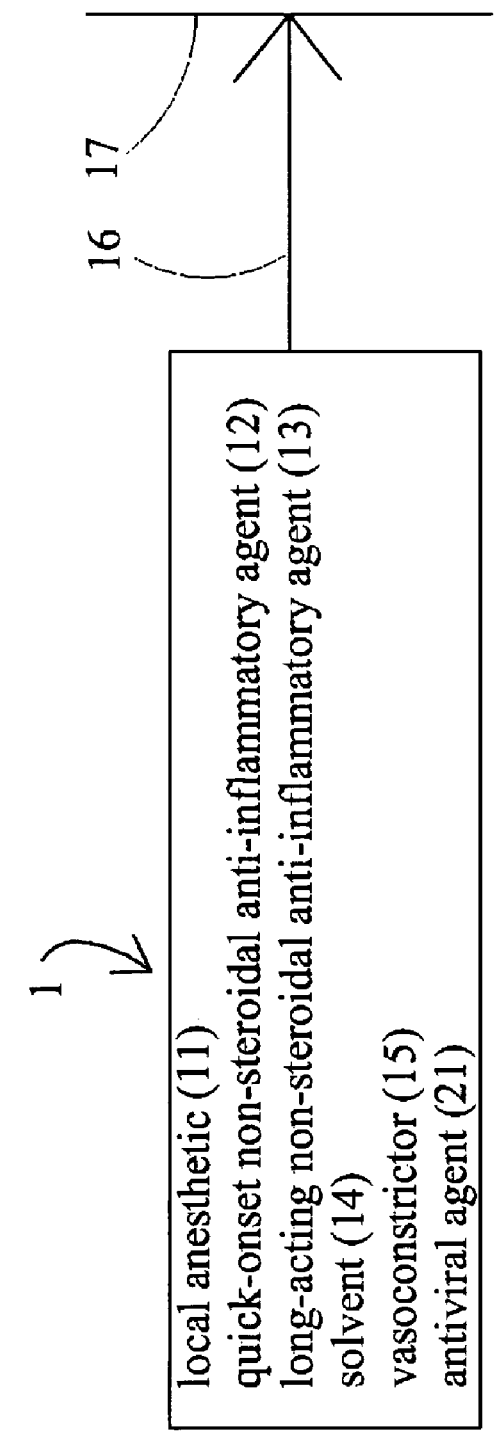

US 7,666,914 B2

TOPICAL PREPARATION AND METHOD FOR TRANSDERMAL DELIVERY AND LOCALIZATION OF THERAPEUTIC AGENTS

FIELD OF THE INVENTION

This invention pertains generally to the medical field of topically-applied therapeutic preparations, and particularly to the transdermal delivery and localization of therapeutic agents, for example, to alleviate pain.

BACKGROUND OF THE INVENTION

Currently there are a number of over-the-counter (OTC) preparations marketed for relief of "minor" muscular aches and pains. None of these agents appears to be effective for moderate-to-severe chronic pain. In fact, it appears that the only topical prescription analgesic specifically marketed for chronic pain is the LIDODERM® Patch which has been available by prescription since the late-1990s.

Notwithstanding the paucity of topical prescription agents currently available for treatment of moderate-to-severe pain (acute, post traumatic, and chronic), a number of factors make utilization of such preparations attractive and advantageous.

In particular, it would be desirable to have available for the relief of moderate-to-severe pain, an analgesic preparation which may be applied directly to the locus of pain and/or proximate the spinal column for nerves involved in the particular pain under treatment.

It would further be desirable for this preparation to avoid the systemic effects of analgesic and adjuvant agents, by relieving moderate-to-severe pain while reducing or eliminating systemic analgesics, e.g., non-steroidal anti-inflammatory drugs (NSAIDs) and/or opiates.

It would further be desirable to provide local anesthetic neural blockade over a sustained and ongoing period without associated appliances (e.g. indwelling catheters) and/or without motor or sympathetic nerve blockade.

It would further be desirable to relieve moderate-to-severe pain with a reduced dosage frequency.

Finally, it would be desirable more generally to provide topical preparations and generalized methods which allow therapeutic agents to be delivered by topical application to a patient's skin, such that after penetrating the skin, dispersion of the therapeutic agent is retarded, and prolonged localized effect is thereby achieved.

Currently, there do not appear to exist products which can achieve these desirable results, and do so with a satisfactory degree of safety and reliability.

SUMMARY OF THE INVENTION

Disclosed herein is a preparation for topically delivering and localizing therapeutic agents, comprising: a vasoconstrictor for retarding vascular dispersion of a therapeutic agent; and a penetration enhancer for facilitating penetration of the vasoconstrictor and the therapeutic agent through a patient's skin.

Further disclosed is an associated method of topically delivering and localizing therapeutic agents, comprising the steps of: using a vasoconstrictor for retarding vascular dispersion of a therapeutic agent; in combination with using a penetration enhancer for facilitating penetration of the vasoconstrictor and the therapeutic agent through a patient's skin.

Also disclosed are various courses of treatment which comprise applying the various disclosed combinations of agents to the patient's skin.

BRIEF DESCRIPTION OF THE DRAWINGS

The features of the invention believed to be novel are set forth in the appended claims. The invention, however, together with further objects and advantages thereof, may best be understood by reference to the following description taken in conjunction with the accompanying drawing (s) and appendices summarized below.

FIG. 1 illustrates a preparation in accordance with a first preferred embodiment of the invention, being applied to a pain locus.

FIG. 2 illustrates the preparation of FIG. 1, as further prepared and applied for the treatment of pain from acute herpes zoster.

DETAILED DESCRIPTION

Disclosed herein is method and associated topical preparation by which a variety of therapeutic agents may be delivered by topical application, transmitted into the body through the skin, and then dispersed slowly so that localized therapeutic effects can be maintained for a prolonged period of time and use of these therapeutic agents may be kept at minimum dosages and/or frequency of application.

As used throughout this disclosure, unless otherwise stated, the specification of concentrations is understood to be by weight, in relation to the clinically-utilized preparation. That is, unless otherwise stated, a 5% concentration of a given ingredient would specify that there are to be 5 grams of that ingredient per 100 grams of the final product as utilized for clinical application to a patient Concentrations in pre-mix compositions, not yet diluted to strengths suitable for clinical use, will thus vary upward accordingly, but are still envisioned and encompassed within the scope of this disclosure and its associated claims.

FIG. 1 illustrates a preferred embodiment of the invention, employed as a preparation 1 for alleviating pain. Preparation 1 is topically applied 16 to a patient's skin 17, either at a pain locus, or at a suitable spinal site. This preparation comprises three therapeutic pain agents: a local anesthetic 11; a quick-onset, short-acting non-steroidal anti-inflammatory agent (NSAID) 12; and a long-acting non-steroidal anti-inflammatory agent (NSAID) 13. Preparation 1 further comprises a penetration enhancer 14 for facilitating penetration of local anesthetic 11, quick-onset, short-acting non-steroidal anti-inflammatory agent 12, long-acting non-steroidal anti-inflammatory agent 13 and vasoconstrictor 15 (discussed below) through a patient's skin 17 to sites of desired action. Finally, preparation 1 comprises a vasoconstrictor 15 for retarding vascular dispersion of local anesthetic 11, quick-onset, short-acting non-steroidal anti-inflammatory agent 12 and long-acting non-steroidal anti-inflammatory agent 13 after these have penetrated the skin surface and entered the vascular system.

In the preferred embodiment of pain-relief preparation 1, local anesthetic 11 preferably comprises bupivacaine. For bupivacaine, the onset of action is 2 to 10 minutes, the peak is at 30 to 45 minutes, and the duration of action is 3 to 6 hours. The bupivacaine concentration is preferably approximately 5%. However, the bupivacaine concentration may acceptably range as low as approximately 2%. The bupivacaine concentration may also acceptably range as high as approximately 10%.

The purpose of local anesthetic 11 is to reduce or block neural transmission of pain. Bupivacaine is preferred, because of its distinct physiochemical properties which make it long-acting, well-absorbed through the skin, and which provide it with significant desired differential blocking properties, favoring sensory over motor.

However, local anesthetic 11 may alternatively comprise a number of other agents as well, alternatively to, or in combination with, bupivacaine. These include the following:

Carbocaine, with the generic name mepivacaine. This has an intermediate duration of action. Onset is 3-5 minutes, peak is 15-45 minutes, and duration is 45-90 minutes. This is a shorter duration of action than bupivacaine. If used, the concentration ranges from as low as approximately 1% to as high as approximately 10%, preferably approximately 5%. Mepivacaine is commercially available for injection in 1%, 1.5%, 2% and 3% solutions.

Chirocaine, with the generic name levobupivacaine. If used, the concentration ranges from as low as approximately 0.25% to as high as approximately 10%, preferably approximately 5%. This has a long duration of action. Onset of action is 2-10 minutes, with duration locally 2-4 hours. If used for epidural or peripheral nerve blocks or obstetrical anesthesia, the duration of action is between 3-9 hours.

Naropin, with the generic name ropivacaine. This is another long-acting anesthetic. Onset is 1-15 minutes with peak in 20-45 minutes and duration of action 2-6 hours. If used, the concentration ranges from as low as approximately 0.25% to as high as approximately 10%, preferably approximately 5%. This is available commercially as 2.5, 7.5 and 10 mg/ml injections.

Nesacaine, with the generic name chloroprocaine. This is another short-duration anesthetic. Onset is 6-12 minutes, peak is 10-20 minutes, and duration is 30-60 minutes. If used, the concentration ranges from as low as approximately 0.25% to as high as approximately 15%, preferably approximately 5%. This is available commercially as 1%, 2% and 3% injection.

Novocain, with the generic name procaine. This is another short-duration anesthetic. Onset is 5-10 minutes peak is at less than 30 minutes, duration is less than 2 hours. If used, the concentration ranges from as low as approximately 0.25% to as high as approximately 15%, preferably approximately 7%. This is available as 1%, 2% and 10% injections commercially.

Xylocaine, with the generic name lidocaine. This is another intermediate-duration anesthetic, available as gel or solution to apply topically usually every 3-4 hours to obtain relief of pain. If used, the concentration ranges from as low as approximately 2% to as high as approximately 15%, preferably approximately 5%. Lidocaine is available as a Jelly in 2 and 4% concentrations, and the ointment is available in both 2.5 and 5% concentrations.

In addition, or alternatively to all of the above, local anesthetic 11 may alternatively comprise etidocaine, ropivacaine, benzocaine, tetracaine, prilocalne and/or any other similar agent known at present or which may become known in the future. For all of these local anesthetics, if used, the concentration ranges from as low as approximately 0.25% to as high as approximately 20%, with a preferred concentration to be determined from experimental testing.

In order to provide both quick relief and long-lasting relief, preparation 1 preferably comprises both quick-onset, short-acting non-steroidal anti-inflammatory agent 12; and long-acting non-steroidal anti-inflammatory agent 13. The determining factor in what is quick versus long acting is in frequency of dose or half life of the drug entity. The shorter the half life, the more frequent the dosing. As used herein, quick-onset, non-steroidal anti-inflammatory agent 12 is any NSAID with any oral dosing frequency of more than twice daily. As used herein, a long-acting non-steroidal anti-inflammatory agent 13 is any NSAID with no oral dosing frequency of more than twice daily.

In a preferred embodiment of pain-relief preparation 1, quick-onset, short-acting non-steroidal anti-inflammatory agent 12 preferably comprises ketoprofen. The ketoprofen concentration is preferably approximately 10%. However, the ketoprofen concentration may acceptably range as low as approximately 5%. The ketoprofen concentration may also acceptably range as high as approximately 20%.

The purpose of quick-onset, short-acting non-steroidal anti-inflammatory agent 12 is to quickly prevent, retard, or reverse the inflammatory and/or algesic response in tissues at a site of injury, irritation or disease and/or at a suitable spinal location. Thus, quick-onset, short-acting non-steroidal anti-inflammatory agent 12 may alternatively comprise: diclofenac with a concentration of at least approximately 2% and at most approximately 20%, and with a preferred concentration of approximately 10%; diflunisal with a concentration of at least approximately 5% and at most approximately 20%, with a preferred concentration of approximately 10%; etodolac with a concentration of at least approximately 2% and at most approximately 20%, with a preferred concentration of approximately 10%; fenoprofen with a concentration of at least approximately 10% and at most approximately 30%, with a preferred concentration of approximately 20%; flurbiprofen with a concentration of at least approximately 2% and at most approximately 20%, with a preferred concentration of approximately 10%; ibuprofen with a concentration of at least approximately 5% and at most approximately 30%, with a preferred concentration of approximately 20%; indomethacin with a concentration of at least approximately 2% and at most approximately 20%, with a preferred concentration of approximately 10%; tolmetin with a concentration of at least approximately 2% and at most approximately 20%, with a preferred concentration of approximately 10%, and/or, in suitable concentration, any other similar quick-onset, short-acting non-steroidal anti-inflammatory agent known at present or which may become known in the future.

As among all of the above quick-onset, short-acting NSAIDs, ketoprofen is preferred because it passes most readily through the skin. It is believed that the next best is Ibuprofen, then indomethacin, and then diclofenac.

In the preferred embodiment of pain-relief preparation 1, long-acting non-steroidal anti-inflammatory agent 13 preferably comprises piroxicam. The piroxicam concentration is preferably approximately 1%. However, the piroxicam concentration may acceptably range as low as approximately 0.5%. The piroxicam concentration may also acceptably range as high as approximately 4%.

The purpose of long-acting non-steroidal anti-inflammatory agent 13 is to prevent, retard or reverse inflammatory and algesic response for a more prolonged and sustained duration at a site of injury, irritation or disease, and/or via suitable spinal placement. Thus, in alternative preferred embodiments, long-acting non-steroidal anti-inflammatory agent 13 may alternatively comprise: celecoxib with a concentration of at least approximately 5% and at most approximately 20%, with a preferred concentration of approximately 10%; meloxicam with a concentration of at least approximately 0.5% and at most approximately 2%, with a preferred concentration of approximately 1%; nabumetone with a concentration of at least approximately 5% and at most approximately 20%, with a preferred concentration of approximately 10%; naproxen with a concentration of at least approximately 2% and at most approximately 20%, with a preferred concentration of approximately 10%; oxaprozin with a concentration of at least approximately 5% and at most approximately 20%, with a preferred concentration of approximately 10%; rofecoxib with a concentration of at least approximately 0.5% and at most approximately 2%, with a preferred concentration of approximately 1%; sulindac with a concentration of at least approximately 2% and at most approximately 10%, with a preferred concentration of approximately 5%; valdecoxib with a concentration of at least approximately 0.5% and at most approximately 2%, with a preferred concentration of approximately 1%; and/or, in suitable concentration, any other long-acting non-steroidal anti-inflammatory agent known at present or which may become known in the future.

As among all of the aforementioned long-acting NSAIDs, piroxicam is the most effective long-acting NSAID, has been used for many years with a high degree of safety, and is also among the least expensive.

Please note all three of local anesthetic 11, quick-onset, short-acting non-steroidal anti-inflammatory agent 12, and long-acting non-steroidal anti-inflammatory agent (NSAID) 13 are provided together in preparation 1, because each has distinct effects, onsets, peaks and durations which—together—provide the most effective action against pain. However, if certain agents were presently available or were to be developed in the future which combine the desirable properties of these three agents 11, 12, 13, and can penetrate the skin as will be further discussed below, this disclosure fully envisions the use of such agents, and the ability to thus eliminate one or more of agents 11, 12, 13. Further, in a treatment situation where the combined effects of agents 11, 12, 13 are not all necessary, this disclosure fully envisions that one or two of these agents may be omitted consistent with the treatment that is warranted. Further, it is recognized that some of the particular agents 11, 12, 13 may be suitable for dispensation only by prescription and/or administration only by a physician and that others may be suitably dispensed over-the counter and applied by an unsupervised patient. Thus, the particular choice of agents 11, 12, 13 may in some circumstances depend upon whether distribution is intended to be with or without prescription and whether administration is intended to be with or without physician supervision. All of the above also applies to antiviral agent 21, see below.

In the preferred embodiment of pain-relief preparation 1, penetration enhancer 14 preferably comprises dimethylsulfoxide (DMSO) and/or lecithin. The purpose of penetration enhancer 14 is to carry the therapeutic agents (for example, 11, 12 and/or 13 for the pain preparation of FIG. 1; also 21 for the viral treatment preparation of FIG. 2) and the vasoconstrictor 15 through a patient's skin to sites of desired action.

Ease of transmission through skin is linearly related to concentration of DMSO. Too high a concentration of DMSO, however, causes adverse side effects, specifically malodorous breath. Thus, to enhance transmission through the skin of the therapeutic agents (e.g., 11, 12, 13, and/or 21) and the vasoconstrictor 15 as much as possible, but to avoid the adverse side-effects of DMSO, the DMSO concentration is preferably approximately 10%. The DMSO concentration, however, can also be reduced below 10% to further avoid adverse side effects. Finally, if in the future it becomes possible mitigate the side-effects of DMSO and thus to employ DMSO in concentrations above 10%, this too is a possibility within the scope of this disclosure.

In an alternative, equally preferred embodiment, penetration enhancer 14 comprises lecithin, in a preferred concentration of approximately 10% to 12%, and in an acceptable concentration of at least approximately 2% to 5% and at most approximately 50%. If lecithin is employed, then DMSO can be eliminated entirely, or its concentration reduced well under 10%, because the lecithin itself will enable sufficient transmission of the therapeutic agents (e.g., 11, 12, 13, and/or 21) and the vasoconstrictor 15 through the skin.

Lecithin may optionally be used in combination with ethoxy diglycol, or any similar solvent known or which may become known in the future which that acts to dissolve the active ingredients to allow Lecithin to aid in penetration of the skin.

In alternative preferred embodiments, penetration enhancer 14 may alternatively comprise any other skin penetration enhancers known at present or which may become known in the future, each of can also serve to penetrate the therapeutic agents (e.g., 11, 12, 13, and/or 21) and vasoconstrictor 15 through the skin 17 to the desired sites of action.

In the preferred embodiment of pain-relief preparation 1, vasoconstrictor 15 preferably comprises phenylephrine. The phenylephrine concentration is preferably approximately 0.5%. However, the phenylephrine concentration may acceptably range as low as approximately 0.25%. The phenylephrine concentration may also acceptably range as high as approximately 1.0%.

The purpose of vasoconstrictor 15 is to retard vascular dispersion of the therapeutic components (e.g., 11, 12, 13, and/or 21) from their site of action, thereby prolonging the duration of the therapeutic effect at anatomical peripheral pain locus and/or the chosen spinal region, and reducing the required dosages and/or dosage frequencies. Phenylephrine is preferred, because it is regarded as a very safe agent and has been used safely for many years. However, in alternative preferred embodiments, vasoconstrictor 15 may alternatively comprise: ephedrine sulfate, in a concentration of at least approximately 0.1% and at most approximately 1.25%, with a preferred concentration of approximately 0.5%; epinephrine, in a concentration of at least 0.005% and at most 0.02%, with a preferred concentration of approximately 0.01%; naphazoline, in a concentration of at least 0.01% and at most 0.2%, with a preferred concentration of approximately 0.1%; oxymetazoline, in a concentration of at least 0.01% and at most 0.1%, with a preferred concentration of approximately 0.05%; and/or, in suitable concentration, any other vasoconstrictors known at present or which may become known in the future. Each of these will also serve to prolong the therapeutic effect and reduce necessary dosing by pacing the delivery of the therapeutic agents through vasoconstriction.

The following inert ingredients, for example, not limitation, may also be added to preparation 1 to provide chemical stability and provide for long shelf life: polaxmer 407; distilled water, sorbic acid, and potassium sorbate. These are otherwise not pharmacologically active as therapeutic agents (e.g., to provide pain relief, antiviral effect, etc.), nor are they involved in the transmission of therapeutic agents through the skin, or in causing vasoconstriction.

Additionally, isopropyl palmitate and/or isopropyl myristate are lecithin solubilizers, and thus would likely be employed among the inert ingredients, particularly if penetration enhancer 14 comprises lecithin.

In a further embodiment illustrated in FIG. 2, preparation 1 may be used to treat pain from acute herpes zoster. To achieve this, preparation 1 comprises an antiviral agent 21, in addition to—or alternatively to—therapeutic pain-relieving agents 11, 12, and/or 13.

In this viral-treatment embodiment of preparation 1 illustrated in FIG. 2, antiviral agent 21 preferably comprises 2-deoxy-d-glucose. The 2-deoxy-d-glucose concentration is preferably approximately 0.2%. However, the 2-deoxy-d-glucose concentration may acceptably range as low as approximately 0.1%. The 2-deoxy-d-glucose concentration may also acceptably range as high as approximately 0.4%.

Antiviral agent 21 may comprise any agent commonly used on viruses manifested by skin eruptions. Thus, in alternative preferred embodiments, antiviral agent 21 may alternatively comprise: condylox, with the generic name podofilox, topical, at approximately 0.5% concentration, and a concentration range of at least 0.1% and at most 1%; zovirax, with the generic name acyclovir, cream or ointment, at approximately 5% concentration, and a concentration range of at least 2% and at most 10%; denavir, with the generic name penciclovir, topical, at approximately 1.0% concentration, and a concentration range of at least 0.5% and at most 4%; abreva, with the generic name docosanol, topical, at approximately 10% concentration, and a concentration range of at least 5% and at most 15%; and/or, in suitable concentration, any other topically-usable antiviral agents known at present or which may become known in the future, which may be used to treat viruses manifested by skin eruptions.

As noted earlier, unless otherwise stated, the specification of concentrations throughout this disclosure is understood to be by weight, in relation to the clinically-utilized preparation. However, because the combination of a vasoconstrictor and a penetration enhancer is useful as a base composition for topically delivering and localizing therapeutic agents independent of the particular therapeutic agents chosen, it may be desirable to manufacture a vasoconstrictor for retarding vascular dispersion of at least one therapeutic agent in combination with a penetration enhancer for facilitating penetration of the vasoconstrictor and the at least one therapeutic agent through a patient's skin, without including any therapeutic agent. This base "pre-mix" composition—which is effectively a topical delivery and localization composition—would then be separately compounded with the particular therapeutic agents to be topically-delivered, and diluted to appropriate clinically-utilized concentrations with suitable inert ingredients such as but not limited to those set forth above. The reason that all percentages set forth in this disclosure are in relation to the clinically-utilized preparation is to maintain a consistent and definite baseline for comparing relative concentrations of all ingredients. However, it is to be understood that the specification and claiming of a lower concentration percentage for an ingredient of the clinical preparation scales relatively upward and is also intended to encompass a higher concentration percentage in any pre-mix composition.

Thus, particularly as used in the claims, the term "clinical concentration" refers not only to the particular clinical concentrations specified, but also to "scaled up" concentrations appearing in pre-mix compositions which have not yet fully mixed with all their ingredients and/or diluted down to their ultimate concentrations for clinical use.

Thus, for example, given a preferred DMSOclinical concentration of up to 10% and a preferred phenylephrineclinical concentration ranging from 0.25% to 1.0% as set forth above, it is to be understood that this disclosure and its associated claims would thereby cover any composition comprising DMSO and phenylephrine in a ratio of approximately 40 to 1 (10% to 0.25%) or less. Similarly, for example, given a preferred lecithin concentration of up to 50% and a preferred phenylephrineclinical concentration ranging from 0.25% to 1.0% as set forth above, it is to be understood that this disclosure and its associated claims would thus cover any composition comprising lecithin and phenylephrine in a ratio of approximately 200 to 1 (50% to 0.25%) or less. The same holds true for the relative clinical proportions (ratios) between and among any and all of the many other ingredients also disclosed herein.

While upper concentration limits have been stated herein for the various agents 11, 12, 13, 14, 15, 21, it may turn out following clinical trials that higher limits than those stated can be utilized without adverse patient effect. Thus, it is considered possible to utilize upper concentration limits which are in fact 125%, 150%, 175% and even as much as 200% of the upper concentration limits set forth herein, for all of the agents 11, 12, 13, 14, 15, 21 set forth herein. This is to say, for example, that while the stated upper concentration limit for bupivacaine is 10%, it may turn out to be possible following clinical trials to employ an upper limit of 12.5%, 15%, 17.5%, and even as high as 20%, and that the same multipliers apply to all of the other agents 11, 12, 13, 14, 15, 21 and their upper concentration limits set forth herein. The only exception is lecithin, which already has an upper limit of 50%, and certainly cannot be 100% since that would foreclose the use of any other agents. Rather, Lecithin, as a safe agent, may in fact comprise whatever proportion of preparation 1 is not accounted for by vasoconstrictor 15 and the various therapeutic agents (e.g., 11, 12, 13, 21) employed in any given situation, and in particular, it may well be possible for lecithin to thus account for 60%, 70%, 80%, 90%, 95%, and even more, of the overall preparation 1 in clinical form. That is, lecithin may account for 100%, minus the percentages of vasoconstrictor 15 and all of the various therapeutic agents, of preparation 1.

All of preferred ingredients set forth above for the disclosed embodiments of preparation 1 are readily available and are currently utilized in clinical medical therapeutics in various settings. However, the particular combinations disclosed are novel and non-obvious. Additionally, the particular choices of agents disclosed herein, in the disclosed combinations, and/or in the disclosed clinical and relative concentrations, are also novel and non-obvious.

Preparation 1 in various pain-relief and other embodiments is preferably fabricated and utilized, for example, not limitation, as a topical gel or cream, or with a topical delivery system such as a patch. The topical, e.g., gel or cream is applied 16 directly to the skin 17 at the locus of pain or other ailment to be topically treated, and/or to a suitable spinal location. Sustained effect may be achieved by placing a thin plastic dressing over the applied gel, forming a patch. If applied via a patch, the patch may be pre-fabricated to comprise preparation 1 therein or thereon as a delivery system, so that patch itself may be applied to the skin at the pain locus and/or at a suitable spinal location to alleviate moderate-to-severe pain, and generally at the treatment locus for whatever treatment is being delivered. The e.g., gel or cream may also, of course, be applied to the patch and the patch then applied to the patient's skin.

For pain relief, preparation 1 comprising at least one of agents 11, 12, and/or 13 is applied over exquisitely painful areas of the body. Within 20 to 40 minutes, this provides substantial-to-complete pain relief—relief which may be equivalent to that produced by surgical neural blockade. It may also be applied on intact skin including over healed skin scars (for example, following surgery), and over herpes zoster. Application in various body apertures, e.g., ear, nose, mouth, throat, rectum, etc., as well as application to open wounds which have not yet healed over sufficiently to attain skin integrity, is to be avoided. Thus, as used in this disclosure and its associated claims, the term "patient's skin" is intended to refer to intact skin including skin with healed scars, and to non-open skin with herpes zoster.

Additionally or alternatively, as noted several times above, preparation 1 may be applied—still to a patient's intact skin—along the spinal column where the nerves involved in the particular pain being treated enter the spinal column, thus further relieving areas enervated by those specific nerves. Thus, for example, application of the preparation to the skin overlying various areas of the dorsal spine may relieve pain in the dermatones of the nerve roots most proximal to said application. Placement of preparation 1, e.g., over L 4-5 paravertebral area may relieve lower leg pain ('sciatica'). The same holds true for other areas of the body and other spinal nerves.

In contrast to the invention disclosed herein, the current treatment of moderate-to-severe pain states is often inadequate, despite the use of potent systemic analgesics, including opiate analgesics. Currently, if patients require potent systemic analgesics, or are unable to achieve effective relief, they are rendered partially-to-fully disabled by their pain, are often unable to work or function effectively in domestic settings, and may become prey to all the consequences of severe chronic pain ("Chronic Pain Syndrome").

The pain-relief preparation 1 of FIG. 1 provides clear promise to effectively control severe pain over prolonged periods of time, with consequent improvement in overall patient function, avoidance or reduction in usage of systemic medications, and consequent reduction in the ill effects of such systemic medications.

It is important to point out that the scope of this disclosure encompasses preparation 1 using the various ingredients and concentrations disclosed herein, alone or in combination with patches and other delivery systems. This disclosure also encompasses the methods of use of the various agents in the various combinations disclosed herein. This disclosure also encompasses various methods for alleviating pain by applying preparation 1 (and more generally, topically delivering and localizing therapeutic agents), and prescribing and/or distributing preparation 1 separately or in combination with various delivery systems to alleviate pain (or to provide general therapy).

While only certain preferred features of the invention have been illustrated and described, many modifications, changes and substitutions will occur to those skilled in the art. It is, therefore, to be understood that the appended claims are intended to cover all such modifications and changes as fall within the true spirit of the invention.

The invention claimed is:

1. A preparation for topically delivering and localizing at least one therapeutic agent, comprising:
   a vasoconstrictor for retarding vascular dispersion of a therapeutic agent, selected from the vasoconstrictor group consisting of at least one of: phenylephrine, ephedrine sulfate, epinephrine, naphazoline, and oxymetazoline; and
   a penetration enhancer for facilitating penetration of said vasoconstrictor and said therapeutic agent through a patient's skin, selected from the penetration enhancer group consisting of at least one of: lecithin and dimethylsulfoxide; wherein:
   said therapeutic agent is selected from at least one therapeutic agent in at least one of the following therapeutic agent groups:
   (a) a local anesthetic selected from the group consisting of: bupivacaine, mepivacaine, levobupivacaine, ropivacaine, chloroprocaine, procaine, lidocaine, etidocaine, benzocaine, tetracaine, and prilocaine;
   (b) a quick-onset, short-acting non-steroidal anti-inflammatory agent selected from the group consisting of: ketoprofen, diclofenac, diflunisal, etodolac, fenoprofen, flurbiprofen, ibuprofen, indomethacin, and tolmetin;
   (c) a long-acting non-steroidal anti-inflammatory agent selected from the group consisting of: piroxicam, celecoxib, meloxicam, nabumetone, naproxen, oxaprozin, rofecoxib, sulindac, and valdecoxib;
   (d) an antiviral agent selected from the group consisting of: 2-deoxy-d-glucose, podofilox, acyclovir, penciclovir, and docosanol.

2. The preparation of claim 1, said vasoconstrictor comprising phenylephrine.

3. The preparation of claim 2, wherein:
   a clinical concentration of said phenylephrine is at least approximately 0.125%; and
   said clinical concentration of said phenylephrine is at most approximately 1.0%.

4. The preparation of claim 3, wherein said clinical concentration of said phenylephrine is approximately 0.5%.

5. The preparation of claim 1, said vasoconstrictor comprising a vasoconstrictor selected from the vasoconstrictor group consisting of: ephedrine sulfate, epinephrine, naphazoline, and oxymetazoline.

6. The preparation of claim 1, said penetration enhancer comprising dimethylsulfoxide.

7. The preparation of claim 6, wherein a clinical concentration of said dimetbylsulfoxide is at most approximately 10%.

8. The preparation of claim 7, wherein said clinical concentration of said dimethylsulfoxide is approximately 10%.

9. The preparation of claim 1, said penetration enhancer comprising lecithin.

10. The preparation of claim 9, said penetration enhancer further comprising ethoxy diglycol.

11. The preparation of claim 9, wherein:
    a clinical concentration of said lecithin is at least approximately 2%; and
    said clinical concentration of said lecithin is at most approximately 50%.

12. The preparation of claim 11, wherein:
    said clinical concentration of said lecithin is approximately 10% to 12%.

13. The preparation of claim 1:
    said vasoconstrictor comprising phenylephrine; and
    said penetration enhancer comprising dimethylsulfoxide.

14. The preparation of claim 13, wherein:
    a clinical concentration of said phenylephrine is at least approximately 0.125%;
    said clinical concentration of said phenylephrine is at most approximately 1.0%; and
    a clinical concentration of said dimethylsulfoxide is at most approximately 10%.

15. The preparation of claim 14, wherein:
    said clinical concentration of said phenylephrine is approximately 0.5%; and
    said clinical concentration of said dimethylsulfoxide is approximately 10%.

16. The preparation of claim 13, wherein:
    a ratio of a clinical concentration of said dimethylsulfoxide to a clinical concentration of said phenylephrine is at most approximately 40 to 1.

17. The preparation of claim 1:
    said vasoconstrictor comprising phenylephrine; and
    said penetration enhancer comprising lecithin.

18. The preparation of claim 17, said penetration enhancer further comprising ethoxy diglycol.

19. The preparation of claim 17, wherein:

a clinical concentration of said phenylephrine is at least approximately 0.125%;
said clinical concentration of said phenylephrine is at most approximately 1.0%; and
a clinical concentration of said lecithin is at most approximately 50%.

20. The preparation of claim 19, wherein:
said clinical concentration of said phenylephrine is approximately 0.5%; and
said clinical concentration of said lecithin is approximately 10% to 12%.

21. The preparation of claim 17, wherein:
a ratio of a clinical concentration of said lecithin to a clinical concentration of said phenylephrine is at most approximately 200 to 1.

22. The preparation of claim 1, further comprising:
said therapeutic agent.

23. The preparation of claim 22, particularly for relieving pain, comprising:
said therapeutic agent comprising a therapeutic pain relieving agent;
said penetration enhancer for facilitating penetration of said therapeutic pain-relieving agent and said vasoconstrictor through the patient's skin; and
said vasoconstrictor for retarding vascular dispersion of said therapeutic agent.

24. The preparation of claim 23, said therapeutic pain-relieving agent comprising:
a local anesthetic.

25. The preparation of claim 24, said local anesthetic comprising bupivacaine.

26. The preparation of claim 25, wherein:
a clinical concentration of said bupivacaine is at least approximately 2%; and
said clinical concentration of said bupivacaine is at most approximately 10%.

27. The preparation of claim 26, wherein said clinical concentration of said bupivacaine is approximately 5%.

28. The preparation of claim 24, said local anesthetic comprising a local anesthetic selected from the local anesthetic group consisting of: mepivacaine, levobupivacaine, ropivacaine, chioroprocaine, procaine, lidocaine, etidocaine, benzocaine, tetracaine, and prilocaine.

29. The preparation of claim 23, said therapeutic pain-relieving agent comprising:
a quick-onset, short-acting non-steroidal anti-inflammatory agent.

30. The preparation of claim 29, said quick-onset, short-acting non-steroidal anti-inflammatory agent comprising ketoprofen.

31. The preparation of claim 30, wherein:
a clinical concentration of said ketoprofen is at least approximately 5%; and
said clinical concentration of said ketoprofen is at most approximately 20%.

32. The preparation of claim 31, wherein said clinical concentration of said ketoprofen is approximately 10%.

33. The preparation of claim 29, said quick-onset, short-acting non-steroidal anti-inflammatory agent comprising a quick-onset, short-acting non-steroidal anti-inflammatory agent selected from the quick-onset, short-acting non-steroidal anti-inflammatory agent group consisting of:
diclofenac, diflunisal, etodolac, fenoprofen, flurbiprofen, ibuprofen, indomethacin, and tolmetin.

34. The preparation of claim 23, said therapeutic pain-relieving agent comprising:
a long-acting non-steroidal anti-inflammatory agent.

35. The preparation of claim 34, said long-acting non-steroidal anti-inflammatory agent comprising piroxicam.

36. The preparation of claim 35, wherein:
a clinical concentration of said piroxicam is at least approximately 0.5%; and
said clinical concentration of said piroxicam is at most approximately 4%.

37. The preparation of claim 36, wherein said clinical concentration of said piroxicam is approximately 1.0%.

38. The preparation of claim 34, said long-acting non-steroidal anti-inflammatory agent comprising a long-acting non-steroidal anti-inflammatory agent selected from the long-acting non-steroidal anti-inflammatory agent group consisting of: celecoxib, meloxicam, nabumetone, naproxen, oxaprozin, rofecoxib, sulindac, and valdecoxib.

39. The preparation of claim 23, said therapeutic pain-relieving agent comprising:
a local anesthetic; and
a quick-onset, short-acting non-steroidal anti-inflammatory agent.

40. The preparation of claim 39:
said local anesthetic comprising bupivacaine; and
said quick-onset, short-acting non-steroidal anti-inflammatory agent comprising ketoprofen.

41. The preparation of claim 23, said therapeutic pain-relieving agent comprising:
a local anesthetic; and
a long-acting non-steroidal anti-inflammatory agent.

42. The preparation of claim 41:
said local anesthetic comprising bupivacaine; and
said long-acting non-steroidal anti-inflammatory agent comprising piroxicam.

43. The preparation of claim 23, said therapeutic pain-relieving agent comprising:
a quick-onset, short-acting non-steroidal anti-inflammatory agent; and
a long-acting non-steroidal anti-inflammatory agent.

44. The preparation of claim 43:
said quick-onset, short-acting non-steroidal anti-inflammatory agent comprising ketoprofen; and
said long-acting non-steroidal anti-inflammatory agent comprising piroxicam.

45. The preparation of claim 23, said therapeutic pain-relieving agent comprising:
a local anesthetic;
a quick-onset, short-acting non-steroidal anti-inflammatory agent; and
a long-acting non-steroidal anti-inflammatory agent.

46. The preparation of claim 45:
said local anesthetic comprising bupivacaine;
said quick-onset, short-acting non-steroidal anti-inflammatory agent comprising ketoprofen; and
said long-acting non-steroidal anti-inflammatory agent comprising piroxicam.

47. The preparation of claim 46, wherein:
a clinical concentration of said bupivacaine is at least approximately 2%;
said clinical concentration of said bupivacaine is at most approximately 10%;
a clinical concentration of said ketoprofen is at least approximately 5%;
said clinical concentration of said ketoprofen is at most approximately 20%;
a clinical concentration of said piroxicam is at least approximately 0.5%; and
said clinical concentration of said piroxicam is at most approximately 4%.

48. The preparation of claim 47, wherein:
said clinical concentration of said bupivacaine is approximately 5%;
said clinical concentration of said ketoprofen is approximately 10%; and
said clinical concentration of said piroxicam is approximately 1.0%

49. The preparation of claim 22, particularly for treating a viral disease, comprising:
said therapeutic agent comprising an antiviral agent;
said penetration enhancer for facilitating penetration of said antiviral agent and said vasoconstrictor through the patient's skin; and
said vasoconstrictor for retarding vascular dispersion of said antiviral agent.

50. The preparation of claim 49, said antiviral agent comprising 2-deoxy-d-glucose.

51. The preparation of claim 50, wherein:
a clinical concentration of said 2-deoxy-d-glucose is at least approximately 0.1%; and
said clinical concentration of said 2-deoxy-d-glucose is at most approximately 0.4%.

52. The preparation of claim 51, wherein:
said clinical concentration of said 2-deoxy-d-glucose is approximately 0.2%.

53. The preparation of claim 49, said antiviral agent comprising an antiviral agent selected from the antiviral agent group consisting of: podofilox, acyclovir, penciclovir, and docosanol.

54. The preparation of claim 23, particularly for relieving pain from a viral disease and treating the viral disease, comprising:
said therapeutic agent further comprising an antiviral agent;
said penetration enhancer for further facilitating penetration of said antiviral agent through the patient's skin; and
said vasoconstrictor for further retarding vascular dispersion of said antiviral agent.

55. The preparation of claim 54, said antiviral agent comprising 2-deoxy-d-glucose.

56. The preparation of claim 55, wherein:
a clinical concentration of said 2-deoxy-d-glucose is at least approximately 0.1%; and
said clinical concentration of said 2-deoxy-d-glucose is at most approximately 0.4%.

57. The preparation of claim 56, wherein:
said clinical concentration of said 2-deoxy-d-glucose is approximately 0.2%.

58. The preparation of claim 54, said antiviral agent comprising an antiviral agent selected from the antiviral agent group consisting of: podofilox, acyclovir, penciclovir, and docosanol.

59. The preparation of claim 45:
said vasoconstrictor comprising phenylephrine;
said penetration enhancer comprising a penetration enhancing agent selected from the penetration-enhancing agent group consisting of dimetbylsulfoxide and lecithin;
said local anesthetic comprising bupivacaine;
said quick-onset, short-acting non-steroidal anti-inflammatory agent comprising ketoprofen; and
said long-acting non-steroidal anti-inflammatory agent comprising piroxicam.

60. The preparation of claim 59, wherein:
a clinical concentration of said phenylephrine is at least approximately 0.125%;
said clinical concentration of said phenylephrine is at most approximately 1.0%;
a clinical concentration of said dimethylsulfoxide is at most approximately 10%;
a clinical concentration of said lecithin is at most approximately 50%;
a clinical concentration of said bupivacaine is at least approximately 2%;
said clinical concentration of said bupivacaine is at most approximately 10%;
a clinical concentration of said ketoprofen is at least approximately 5%;
said clinical concentration of said ketoprofen is at most approximately 20%;
a clinical concentration of said piroxicam is at least approximately 0.5%; and
said clinical concentration of said piroxicam is at most approximately 4%.

61. The preparation of claim 60, wherein:
said clinical concentration of said phenylephrine is approximately 0.5%;
said clinical concentration of said bupivacaine is approximately 5%;
said clinical concentration of said ketoprofen is approximately 10%; and
said clinical concentration of said piroxicam is approximately 1.0%.

62. The preparation of claim 45, additionally for treating a viral disease, said therapeutic agent further comprising:
an antiviral agent.

63. The preparation of claim 62:
said vasoconstrictor comprising phenylephrine;
said penetration enhancer comprising a penetration enhancing agent selected from the penetration-enhancing agent group consisting of dimethylsulfoxide and lecithin;
said local anesthetic comprising bupivacaine;
said quick-onset, short-acting non-steroidal anti-inflammatory agent comprising ketoprofen;
said long-acting non-steroidal anti-inflammatory agent comprising piroxicam; and
said antiviral agent comprising 2-deoxy-d-glucose.

64. The preparation of claim 63, wherein:
a clinical concentration of said phenylephrine is at least approximately 0.125%;
said clinical concentration of said phenylephrine is at most approximately 1.0%;
a clinical concentration of said dimethylsulfoxide is at most approximately 10%;
a clinical concentration of said lecithin is at most approximately 50%;
a clinical concentration of said bupivacaine is at least approximately 2%;
said clinical concentration of said bupivacaine is at most approximately 10%;
a clinical concentration of said ketoprofen is at least approximately 5%;
said clinical concentration of said ketoprofen is at most approximately 20%;
a clinical concentration of said piroxicam is at least approximately 0.5%;
said clinical concentration of said piroxicam is at most approximately 4%;
a clinical concentration of said 2-deoxy-d-glucose is at least approximately 0.1%; and
said clinical concentration of said 2-deoxy-d-glucose is at most approximately 0.4%.

65. The preparation of claim 64, wherein:
said clinical concentration of said phenylephrine is approximately 0.5%;
said clinical concentration of said bupivacaine is approximately 5%;
said clinical concentration of said ketoprofen is approximately 10%;
said clinical concentration of said piroxicam is approximately 1.0%; and
said clinical concentration of said 2-deoxy-d-glucose is approximately 0.2%.

66. A method of topically delivering and localizing at least one therapeutic agent, comprising:
using a vasoconstrictor for retarding vascular dispersion of a therapeutic agent, selected from the vasoconstrictor group consisting of at least one of: phenylephrine, ephedrine sulfate, epinephrine, naphazoline, and oxymetazoline; in combination with
using a penetration enhancer for facilitating penetration of said vasoconstrictor and said therapeutic agent through a patient's skin, selected from the penetration enhancer group consisting of at least one of: lecithin and dimethylsulfoxide; wherein:
said therapeutic agent is selected from at least one therapeutic agent in at least one of the following therapeutic agent groups:
(a) a local anesthetic selected from the group consisting of: bupivacaine, mepivacaine, levobupivacaine, ropivacaine, chioroprocaine, procaine, lidocaine, etidocaine, benzocaine, tetracaine, and prilocaine;
(b) a quick-onset, short-acting non-steroidal anti-inflammatory agent selected from the group consisting of: ketoprofen, diclofenac, diflunisal, etodolac, fenoprofen, flurbiprofen, ibuprofen, indomethacin, and tolmetin;
(c) a long-acting non-steroidal anti-inflammatory agent selected from the group consisting of: piroxicam, celecoxib, meloxicam, nabumetone, naproxen, oxaprozin, rofecoxib, sulindac, and valdecoxib; (d) an antiviral agent selected from the group consisting of: 2-deoxy-d-glucose, podofilox, acyclovir, penciclovir, and docosanol.

67. The method of claim 66, said using said vasoconstrictor further comprising using phenylephrine.

68. The method of claim 67, further comprising:
using a clinical concentration of said phenylephrine, of at least approximately 0.125%; and
using said clinical concentration of said phenylephrine, of at most approximately 1.0%.

69. The method of claim 68, further comprising using said clinical concentration of said phenylephrine, of approximately 0.5%.

70. The method of claim 66, said using said vasoconstrictor further comprising using a vasoconstrictor selected from the vasoconstrictor group consisting of: ephedrine sulfate, epinephrine, naphazoline, and oxymetazoline.

71. The method of claim 66, said using said penetration enhancer further comprising using dimethylsulfoxide.

72. The method of claim 71, further comprising using a clinical concentration of said dimethylsulfoxide, of at most approximately 10%.

73. The method of claim 72, further comprising using said clinical concentration of said dimethylsulfoxide, of approximately 10%.

74. The method of claim 66, said using said penetration enhancer further comprising using comprising lecithin.

75. The method of claim 74, said using said penetration enhancer further comprising using ethoxy diglycol.

76. The method of claim 74, further comprising:
using a clinical concentration of said lecithin, of at least approximately 2%; and
using said clinical concentration of said lecithin, of at most approximately 50%.

77. The method of claim 76, further comprising:
using said clinical concentration of said lecithin, of approximately 10% to 12%.

78. The method of claim 66:
said using said vasoconstrictor further comprising using phenylephrine; and
said using said penetration enhancer further comprising using dimethylsulfoxide.

79. The method of claim 78, further comprising:
using a clinical concentration of said phenylephrine, of at least approximately 0.125%;
using said clinical concentration of said phenylephrine, of at most approximately 1.0%; and
using a clinical concentration of said dimethylsulfoxide, of at most approximately 10%.

80. The method of claim 79, further comprising:
using said clinical concentration of said phenylephrine, of approximately 0.5%; and
using said clinical concentration of said dimethylsulfoxide, of approximately 10%.

81. The method of claim 78, further comprising:
using a ratio of a clinical concentration of said dimethylsulfoxide to a clinical concentration of said phenylephrine, of at most approximately 40 to 1.

82. The method of claim 66:
said using said vasoconstrictor further comprising using phenylephrine; and
said using said penetration enhancer further comprising the step of using lecithin.

83. The method of claim 82, said using said penetration enhancer further comprising using ethoxy diglycol.

84. The method of claim 82, further comprising:
using a clinical concentration of said phenylephrine, of at least approximately 0.125%;
using said clinical concentration of said phenylephrine, of at most approximately 1.0%; and
using a clinical concentration of said lecithin, of at most approximately 50%.

85. The method of claim 84, further comprising:
using said clinical concentration of said phenylephrine, of approximately 0.5%; and
using said clinical concentration of said lecithin, of approximately 10% to 12%.

86. The method of claim 82, further comprising:
using a ratio of a clinical concentration of said lecithin to a clinical concentration of said phenylephrine, of at most approximately 200 to 1.

87. The method of claim 66, further comprising:
using said therapeutic agent in combination with using said vasoconstrictor and using said penetration enhancer.

88. The method of claim 87, particularly for relieving pain:
said using said therapeutic agent further comprising using a therapeutic pain-relieving agent;
further comprising:
using said penetration enhancer for facilitating penetration of said therapeutic pain-relieving agent and said vasoconstrictor through the patient's skin; and
using said vasoconstrictor for retarding vascular dispersion of said therapeutic agent.

89. The method of claim 88, said using said therapeutic pain-relieving agent further comprising using a local anesthetic.

90. The method of claim 89, said using said local anesthetic further comprising using bupivacaine.

91. The method of claim 90, further comprising:
using a clinical concentration of said bupivacaine, of at least approximately 2%; and
using said clinical concentration of said bupivacaine, of at most approximately 10%.

92. The method of claim 91, further comprising the step of using said clinical concentration of said bupivacaine, of approximately 5%.

93. The method of claim 89, said using said local anesthetic further comprising using a local anesthetic selected from the local anesthetic group consisting of: mepivacaine, levobupivacaine, ropivacaine, chioroprocaine, procaine, lidocaine, etidocaine, benzocaine, tetracaine, and prilocaine.

94. The method of claim 88, said using said therapeutic pain-relieving agent further comprising using a quick-onset, short-acting non-steroidal anti-inflammatory agent.

95. The method of claim 94, said using said quick-onset, short-acting non-steroidal anti-inflammatory agent further comprising using ketoprofen.

96. The method of claim 95, further comprising:
using a clinical concentration of said ketoprofen, of at least approximately 5%; and
said clinical concentration of said ketoprofen, of at most approximately 20%.

97. The method of claim 96, further comprising using said clinical concentration of said ketoprofen, of approximately 10%.

98. The method of claim 94, said using said quick-onset, short-acting non-steroidal anti-inflammatory agent further comprising using a quick-onset, short-acting non-steroidal anti-inflammatory agent selected from the quick-onset, short-acting non-steroidal anti-inflammatory agent group consisting of: diclofenac, diflunisal, etodolac, fenoprofen, flurbiprofen, ibuprofen, indomethacin, and tolmetin.

99. The method of claim 88, said using said therapeutic pain-relieving agent further comprising using a long-acting non-steroidal anti-inflammatory agent.

100. The method of claim 99, said using said long-acting non-steroidal anti-inflammatory agent further comprising using piroxicam.

101. The method of claim 100, further comprising:
using a clinical concentration of said piroxicam, of at least approximately 0.5%; and
using said clinical concentration of said piroxicam, of at most approximately 4%.

102. The method of claim 101, further comprising using said clinical concentration of said piroxicam, of approximately 1.0%.

103. The method of claim 99, said using said long-acting non-steroidal anti-inflammatory agent further comprising using a long-acting non-steroidal anti-inflammatory agent selected from the long-acting non-steroidal anti-inflammatory agent group consisting of: celecoxib, meloxicam, nabumetone, naproxen, oxaprozin, rofecoxib, sulindac, and valdecoxib.

104. The method of claim 88, said using said therapeutic pain-relieving agent further comprising:
using a local anesthetic; and
using a quick-onset, short-acting non-steroidal anti-inflammatory agent.

105. The method of claim 104:
said using said local anesthetic further comprising using bupivacaine; and
said using said quick-onset, short-acting non-steroidal anti-inflammatory agent further comprising using ketoprofen.

106. The method of claim 88, said using said therapeutic pain-relieving agent further comprising:
using a local anesthetic; and
using a long-acting non-steroidal anti-inflammatory agent.

107. The method of claim 106:
said using said local anesthetic further comprising using bupivacaine; and
said using said long-acting non-steroidal anti-inflammatory agent further comprising using piroxicam.

108. The method of claim 88, said using said therapeutic pain-relieving agent further comprising:
using a quick-onset, short-acting non-steroidal anti-inflammatory agent; and
using a long-acting non-steroidal anti-inflammatory agent.

109. The method of claim 108:
said using said quick-onset, short-acting non steroidal anti-inflammatory agent further comprising using ketoprofen; and
said using said long-acting non-steroidal anti-inflammatory agent further comprising using piroxicam.

110. The method of claim 88, said using said therapeutic pain-relieving agent further comprising:
using a local anesthetic;
using a quick-onset, short-acting non-steroidal anti-inflammatory agent; and
using a long-acting non-steroidal anti-inflammatory agent.

111. The method of claim 110:
said using said local anesthetic further comprising using bupivacaine;
said using said quick-onset, short-acting non-steroidal anti-inflammatory agent further comprising using ketoprofen; and
said using said long-acting non-steroidal anti-inflammatory agent further comprising using piroxicam.

112. The method of claim 111, further comprising:
using a clinical concentration of said bupivacaine, of at least approximately 2%;
using said clinical concentration of said bupivacaine, of at most approximately 10%;
using a clinical concentration of said ketoprofen, of at least approximately 5%;
using said clinical concentration of said ketoprofen, of at most approximately 20%;
using a clinical concentration of said piroxicam, of at least approximately 0.5%; and
using said clinical concentration of said piroxicam, of at most approximately 4%.

113. The method of claim 112, further comprising:
using said clinical concentration of said bupivacaine, of approximately 5%;
using said clinical concentration of said ketoprofen, of approximately 10%; and
using said clinical concentration of said piroxicam, of approximately 1.0%.

114. The method of claim 87, particularly for treating a viral disease:
said using said therapeutic agent further comprising using an antiviral agent; further comprising:
using said penetration enhancer for facilitating penetration of said antiviral agent and said vasoconstrictor through the patient's skin; and
using said vasoconstrictor for retarding vascular dispersion of said antiviral agent.

115. The method of claim 114, said using said antiviral agent further comprising using 2-deoxy-d-glucose.

116. The method of claim 115, further comprising:
using a clinical concentration of said 2-deoxy-d-glucose, of at least approximately 0.1%; and
using said clinical concentration of said 2-deoxy-d-glucose, of at most approximately 0.4%.

117. The method of claim 116, further comprising:
using said clinical concentration of said 2-deoxy-d-glucose, of approximately 0.2%.

118. The method of claim 114, said using said antiviral agent further comprising using an antiviral agent selected from the antiviral agent group consisting of: podofilox, acyclovir, penciclovir, and docosanol.

119. The method of claim 88, particularly for relieving pain from a viral disease and treating the viral disease:
said using said therapeutic agent further comprising using an antiviral agent; further comprising:
using said penetration enhancer for further facilitating penetration of said antiviral agent through the patient's skin; and
using said vasoconstrictor for further retarding vascular dispersion of said antiviral agent.

120. The method of claim 119, said using said antiviral agent further comprising using 2-deoxy-d-glucose.

121. The method of claim 120, further comprising:
using a clinical concentration of said 2-deoxy-d-glucose, of at least approximately 0.1%; and
using said clinical concentration of said 2-deoxy-d-glucose, of at most approximately 0.4%.

122. The method of claim 121, further comprising:
using said clinical concentration of said 2-deoxy-d-glucose, of approximately 0.2%.

123. The method of claim 119, said using said antiviral agent further comprising using an antiviral agent selected from the antiviral agent group consisting of: podofilox, acyclovir, penciclovir, and docosanol.

124. The method of claim 110:
said using said vasoconstrictor further comprising using phenylephrine;
said using said penetration enhancer further comprising using a penetration enhancing agent selected from the penetration-enhancing agent group consisting of dimethylsulfoxide and lecithin;
said using said local anesthetic further comprising using bupivacaine;
said using said quick-onset, short-acting non-steroidal anti-inflammatory agent further comprising using ketoprofen; and
said using said long-acting non-steroidal anti-inflammatory agent further comprising using piroxicam.

125. The method of claim 124, further comprising:
using a clinical concentration of said phenylephrine, of at least approximately 0.125%;
using said clinical concentration of said phenylephrine, of at most approximately 1.0%;
using a clinical concentration of said dimethylsulfoxide, of at most approximately 10%;
using a clinical concentration of said lecithin, of at most approximately 50%;
using a clinical concentration of said bupivacaine, of at least approximately 2%;
using said clinical concentration of said bupivacaine, of at most approximately 10%;
using a clinical concentration of said ketoprofen, of at least approximately 5%;
using said clinical concentration of said ketoprofen, of at most approximately 20%;
using a clinical concentration of said piroxicam, of at least approximately 0.5%; and
using said clinical concentration of said piroxicam, of at most approximately 4%.

126. The method of claim 125, further comprising:
using said clinical concentration of said phenylephrine, of approximately 0.5%;
using said clinical concentration of said bupivacaine, of approximately 5%;
using said clinical concentration of said ketoprofen, of approximately 10%; and
using said clinical concentration of said piroxicam, of approximately 1.0%.

127. The method of claim 110, additionally for treating a viral disease, said using said therapeutic agent further comprising using an antiviral agent.

128. The method of claim 127:
said using said vasoconstrictor further comprising using phenylephrine;
said using said penetration enhancer further comprising using a penetration enhancing agent selected from the penetration-enhancing agent group consisting of dimethylsulfoxide and lecithin;
said using said local anesthetic further comprising using bupivacaine;
said using said quick-onset, short-acting non-steroidal anti-inflammatory agent further comprising using ketoprofen;
said using said long-acting non-steroidal anti-inflammatory agent further comprising using piroxicam; and
said using said antiviral agent further comprising using 2-deoxy-d-glucose.

129. The method of claim 128, further comprising:
using a clinical concentration of said phenylephrine, of at least approximately 0.125%;
using said clinical concentration of said phenylephrine, of at most approximately 1.0%;
using a clinical concentration of said dimethylsulfoxide, of at most approximately 10%;
using a clinical concentration of said lecithin, of at most approximately 50%;
using a clinical concentration of said bupivacaine, of at least approximately 2%;
using said clinical concentration of said bupivacaine, of at most approximately 10%;
using a clinical concentration of said ketoprofen, of at least approximately 5%;
using said clinical concentration of said ketoprofen, of at most approximately 20%;
using a clinical concentration of said piroxicam, of at least approximately 0.5%;
using said clinical concentration of said piroxicam, of at most approximately 4%;
using a clinical concentration of said 2-deoxy-d-glucose, of at least approximately 0.1%; and
using said clinical concentration of said 2-deoxy-d-glucose, of at most approximately 0.4%.

130. The method of claim 129, further comprising:
using said clinical concentration of said phenylephrine, of approximately 0.5%;
using said clinical concentration of said bupivacaine, of approximately 5%;
using said clinical concentration of said ketoprofen, of approximately 10%;

using said clinical concentration of said piroxicam, of approximately 1.0%; and using said clinical concentration of said 2-deoxy-d-glucose, of approximately 0.2%.

131. The method of claim 66, further comprising:

applying said vasoconstrictor and said penetration enhancer to the patient's skin.

132. The method of claim 78, further comprising:

applying said phenylephrine and said dimethylsulfoxide to the patient's skin.

133. The method of claim 82, further comprising:

applying said phenylephrine and said lecithin to the patient's skin.

134. The method of claim 87, further comprising:

applying said vasoconstrictor, said penetration enhancer, and said therapeutic agent to the patient's skin.

135. The method of claim 88, further comprising:

applying said vasoconstrictor, said penetration enhancer, and said therapeutic pain-relieving agent to the patient's skin.

136. The method of claim 89, further comprising:

applying said vasoconstrictor, said penetration enhancer, and said local anesthetic to the patient's skin.

137. The method of claim 90, further comprising:

applying said vasoconstrictor, said penetration enhancer, and said bupivacaine to the patient's skin.

138. The method of claim 94, further comprising:

applying said vasoconstrictor, said penetration enhancer, and said quick-onset, short-acting non-steroidal anti-inflammatory agent to the patient's skin.

139. The method of claim 95, further comprising:

applying said vasoconstrictor, said penetration enhancer, and said ketoprofen to the patient's skin.

140. The method of claim 99, further comprising:

applying said vasoconstrictor, said penetration enhancer, and said long-acting non-steroidal anti-inflammatory agent to the patient's skin.

141. The method of claim 100, further comprising:

applying said vasoconstrictor, said penetration enhancer, and said piroxicam to the patient's skin.

142. The method of claim 110, further comprising:

applying said vasoconstrictor, said penetration enhancer, said local anesthetic, said quick-onset, short-acting non-steroidal anti-inflammatory agent, and said long-acting non-steroidal anti-inflammatory agent to the patient's skin.

143. The method of claim 111, further comprising:

applying said vasoconstrictor, said penetration enhancer, said bupivacaine, said ketoprofen, and said piroxicam to the patient's skin.

144. The method of claim 114, further comprising:

applying said vasoconstrictor, said penetration enhancer, and said antiviral agent to the patient's skin.

145. The method of claim 115, further comprising:

applying said vasoconstrictor, said penetration enhancer, and said 2-deoxy-d-glucose to the patient's skin.

146. The method of claim 119, further comprising:

applying said vasoconstrictor, said penetration enhancer, therapeutic pain-relieving agent, and said antiviral agent to the patient's skin.

147. The method of claim 120, further comprising:

applying said vasoconstrictor, said penetration enhancer, therapeutic pain-relieving agent, and said 2-deoxy-d-glucose to the patient's skin.

148. The method of claim 124, further comprising:

applying said phenylephrine, said penetration enhancing agent selected from the penetration-enhancing agent group consisting of dimethylsulfoxide and lecithin, said bupivacaine, said ketoprofen, and said piroxicam to the patient's skin.

149. The method of claim 127, further comprising:

applying said vasoconstrictor, said penetration enhancer, said local anesthetic, said quick-onset, short-acting non-steroidal anti-inflammatory agent, said long-acting non-steroidal anti-inflammatory agent, and said antiviral agent to the patient's skin.

150. The method of claim 128, further comprising:

applying said phenylephrine, said penetration enhancing agent selected from the penetration-enhancing agent group consisting of dimethylsulfoxide and lecithin, said bupivacaine, said ketoprofen, said piroxicam; and said 2-deoxy-d-glucose to the patient's skin.

* * * * *